United States Patent
King et al.

(10) Patent No.: US 7,938,861 B2
(45) Date of Patent: May 10, 2011

(54) IMPLANTABLE ORTHOPAEDIC DEVICE AND METHOD FOR MAKING THE SAME

(75) Inventors: Richard King, Warsaw, IN (US); Mark Hanes, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 1012 days.

(21) Appl. No.: 10/413,765

(22) Filed: Apr. 15, 2003

(65) Prior Publication Data

US 2004/0210316 A1    Oct. 21, 2004

(51) Int. Cl.
*A61F 2/34* (2006.01)

(52) U.S. Cl. .................................. 623/18.11

(58) Field of Classification Search ........... 623/18.11, 623/22.11, 22.13–22.15, 22.21, 26, 22.3, 623/33, 23.29–30, 23.36, 40, 23.43, 23.5, 623/23.55, 23.57–23.59, 22.26, 22.33, 23.3, 623/23.4

See application file for complete search history.

(56) References Cited

U.S. PATENT DOCUMENTS

| | | |
|---|---|---|
| 2,948,666 A | 11/1956 | Lawton |
| 3,297,641 A | 1/1967 | Werber |
| 3,352,818 A | 11/1967 | Meyer |
| 3,646,155 A | 2/1972 | Scott |
| 3,671,477 A | 6/1972 | Nesbitt |
| 3,758,273 A | 9/1973 | Johnston |
| 3,944,536 A | 3/1976 | Lupton et al. |
| 4,055,862 A | 11/1977 | Farling |
| 4,138,382 A | 2/1979 | Polmanteer |
| 4,179,485 A * | 12/1979 | Tritten .................. 264/628 |
| 4,280,233 A * | 7/1981 | Raab .................. 623/23.59 |
| 4,281,420 A * | 8/1981 | Raab ..................... 128/898 |
| 4,366,618 A | 1/1983 | Lakes |
| 4,390,666 A | 6/1983 | Moriguchi et al. |
| 4,454,612 A * | 6/1984 | McDaniel et al. ...... 623/23.37 |
| 4,483,333 A | 11/1984 | Wartman |
| 4,518,552 A | 5/1985 | Matsuo et al. |
| 4,539,374 A | 9/1985 | Fenton et al. |
| 4,554,612 A | 11/1985 | Childs |
| 4,582,656 A | 4/1986 | Hoffmann |
| 4,586,995 A | 5/1986 | Randall et al. |
| 4,655,769 A | 4/1987 | Zachariades |
| 4,668,527 A | 5/1987 | Fujita et al. |
| 4,715,860 A * | 12/1987 | Amstutz et al. ......... 623/22.33 |

(Continued)

FOREIGN PATENT DOCUMENTS

BE    1001574    12/1989

(Continued)

OTHER PUBLICATIONS

Matsubara, K et al., "The Wear Properties of High-Density Polyethylene Irradiated by Gamma Rays", Wear 10: 214 (1967).

(Continued)

*Primary Examiner* — Eduardo C Robert
*Assistant Examiner* — David Comstock
(74) *Attorney, Agent, or Firm* — Barnes & Thornburg LLP (57) ABSTRACT

A polymeric implantable orthopaedic device that includes a first layer and a second layer where the first layer has a porosity that is different from the second layer is described. An associated method of producing a polymeric implantable orthopaedic device that includes a first layer and a second layer where the first layer has a porosity that is different from the second layer is also described.

14 Claims, 6 Drawing Sheets

U.S. PATENT DOCUMENTS

| | | | |
|---|---|---|---|
| 4,743,493 A | | 5/1988 | Sioshansi et al. |
| 4,747,990 A | | 5/1988 | Gaussens et al. |
| 4,778,474 A | * | 10/1988 | Homsy ............... 623/22.14 |
| 4,816,517 A | | 3/1989 | Wilkus et al. |
| 4,876,049 A | | 10/1989 | Aoyama et al. |
| 4,888,369 A | | 12/1989 | Moore, Jr. |
| 4,902,460 A | | 2/1990 | Yagi et al. |
| 4,944,974 A | | 7/1990 | Zachariades |
| 4,969,910 A | * | 11/1990 | Frey et al. ............. 623/22.33 |
| 5,014,494 A | | 5/1991 | George |
| 5,024,670 A | | 6/1991 | Smith et al. |
| 5,037,928 A | | 8/1991 | Li et al. |
| 5,130,376 A | | 7/1992 | Shih |
| 5,133,757 A | | 7/1992 | Sioshansi et al. |
| 5,137,688 A | | 8/1992 | DeRudder |
| 5,153,039 A | | 10/1992 | Porter et al. |
| 5,160,464 A | | 11/1992 | Ward et al. |
| 5,160,472 A | | 11/1992 | Zachariades |
| 5,180,394 A | | 1/1993 | Davidson |
| 5,192,323 A | | 3/1993 | Shetty et al. |
| 5,200,439 A | | 4/1993 | Asanuma |
| 5,210,130 A | | 5/1993 | Howard, Jr. |
| 5,236,563 A | | 8/1993 | Loh |
| 5,356,998 A | | 10/1994 | Hobes |
| 5,407,623 A | | 4/1995 | Zachariades et al. |
| 5,414,049 A | | 5/1995 | Sun et al. |
| 5,439,949 A | | 8/1995 | Lucas et al. |
| 5,449,745 A | | 9/1995 | Sun et al. |
| 5,464,440 A | * | 11/1995 | Johansson ............. 623/23.55 |
| 5,466,530 A | | 11/1995 | England et al. |
| 5,478,906 A | | 12/1995 | Howard, Jr. |
| 5,480,683 A | | 1/1996 | Chabrol et al. |
| 5,508,319 A | | 4/1996 | DeNicola, Jr. et al. |
| 5,515,590 A | | 5/1996 | Pienkowski |
| 5,543,471 A | | 8/1996 | Sun et al. |
| 5,549,697 A | * | 8/1996 | Caldarise ............... 623/22.26 |
| 5,549,698 A | | 8/1996 | Averill et al. |
| 5,549,700 A | * | 8/1996 | Graham et al. ........... 623/22.14 |
| 5,577,368 A | | 11/1996 | Hamilton et al. |
| 5,593,719 A | | 1/1997 | Dearnaley et al. |
| 5,607,518 A | | 3/1997 | Hoffman et al. |
| 5,609,638 A | | 3/1997 | Price et al. |
| 5,645,594 A | * | 7/1997 | Devanathan et al. ...... 623/11.11 |
| 5,645,882 A | | 7/1997 | Llanos |
| 5,650,485 A | | 7/1997 | Sun et al. |
| 5,674,293 A | | 10/1997 | Armini et al. |
| 5,702,448 A | | 12/1997 | Buechel et al. |
| 5,702,456 A | | 12/1997 | Pienkowski |
| 5,709,020 A | | 1/1998 | Pienkowski et al. |
| 5,728,748 A | | 3/1998 | Sun et al. |
| 5,753,182 A | | 5/1998 | Higgins |
| 5,874,123 A | * | 2/1999 | Park ........................... 427/2.24 |
| 5,876,453 A | | 3/1999 | Beaty |
| 5,879,388 A | * | 3/1999 | Pienkowski et al. ....... 623/18.11 |
| 5,879,398 A | * | 3/1999 | Swarts et al. ............. 623/22.21 |
| 5,879,400 A | | 3/1999 | Merrill et al. |
| 5,879,404 A | * | 3/1999 | Bateman et al. ........... 623/22.21 |
| 5,879,407 A | | 3/1999 | Waggener |
| 5,969,020 A | | 10/1999 | Shalaby et al. |
| 6,017,975 A | | 1/2000 | Saum et al. |
| 6,087,553 A | * | 7/2000 | Cohen et al. ............. 623/22.21 |
| 6,139,322 A | | 10/2000 | Liu |
| 6,143,232 A | | 11/2000 | Rohr |
| 6,165,220 A | * | 12/2000 | McKellop et al. ............ 128/898 |
| 6,168,626 B1 | | 1/2001 | Hyon et al. |
| 6,203,844 B1 | * | 3/2001 | Park ........................... 427/2.26 |
| 6,228,900 B1 | | 5/2001 | Shen et al. |
| 6,245,276 B1 | | 6/2001 | McNulty et al. |
| 6,312,470 B1 | * | 11/2001 | Malawer ............... 623/18.11 |
| 6,316,158 B1 | | 11/2001 | Saum et al. |
| 6,558,428 B2 | * | 5/2003 | Park ........................... 623/23.59 |
| 6,818,172 B2 | * | 11/2004 | King et al. ................... 264/479 |
| 6,827,742 B2 | * | 12/2004 | Hayes et al. ............... 623/22.28 |
| 2002/0016635 A1 | * | 2/2002 | Despres et al. ............ 623/23.5 |
| 2002/0151983 A1 | * | 10/2002 | Shetty ....................... 623/23.5 |
| 2003/0013781 A1 | | 1/2003 | Merrill et al. |
| 2005/0146070 A1 | * | 7/2005 | Muratoglu et al. ............ 264/85 |

FOREIGN PATENT DOCUMENTS

| | | |
|---|---|---|
| EP | 0 169 259 | 1/1985 |
| EP | 0145339 | 6/1985 |
| EP | 0 145 339 B1 | 5/1988 |
| EP | 0 373 800 | 6/1990 |
| EP | 0 722 973 | 7/1996 |
| EP | 0 729 981 | 9/1996 |
| EP | 0 737 481 | 10/1996 |
| EP | 09122222 | 5/1997 |
| EP | 0 803 234 | 10/1997 |
| EP | 0 963 824 | 12/1999 |
| EP | 0 963 824 | 9/2001 |
| JP | 58-157830 | 9/1983 |
| JP | 60135045 | 11/1983 |
| JP | 59168050 | 9/1984 |
| JP | 62243634 | 1/1987 |
| JP | 4-198242 | 7/1992 |
| JP | 4185651 | 7/1992 |
| WO | WO 93/10953 | 6/1993 |
| WO | WO 95/21212 | 8/1995 |
| WO | WO 96/09330 | 3/1996 |
| WO | WO 97/29793 | 8/1997 |
| WO | WO 98/01085 | 1/1998 |
| WO | WO 98/14223 | 4/1998 |
| WO | WO 98/29145 | 7/1998 |
| WO | WO 02/00275 A1 | 1/2002 |

OTHER PUBLICATIONS

Shen, F-S. et al., "Irradiation of Chemically Crosslinked Ultrahigh Molecular Weight Polyethylene", J. Polymer Sci.: Part B: Polymer Phys. 34: 1063-1077 (1996).

Oka, M. et al., "Wear-Resistant Properties of Newly Improved UHMWPE", Trans. Fifth World Biomaterials Congress, Toronto, Canada 520, (May 29-Jun. 2, 1996).

Bellare, A. et al., "Deformation, Morphology and Wear Behavior of Polyethylene", Trans. 23$^{rd}$ Ann. Mtg., Soc. Biomaterials, New Orleans, Louisiana, 75 (Apr. 30-May 4, 1997).

Clarke, I.C. et al., "Simulator Wear Study of High-Dose Gamma-Irradiated UHMWPE Cups", Trans. 23$^{rd}$. Ann. Mtg., Soc. Biomaterials, New Orleans, LA, 71, (Apr. 30-May 4, 1997).

Taylor, G. et al., "Stability of $N_2$ Packaged Gamma Irradiated UHMWPE", Trans. 23$^{rd}$ Ann. Mtg., Soc. Biomaterials, New Orleans, LA, 421, (Apr. 30-May 4, 1997).

Taylor, G. et al., "Stability of $N_2$ Packaged Gamma Irradiated UHMWPE", Trans. 43$^{rd}$ Ann. Mtg., Orthopaedic Res. Soc., San Francisco, California, 776 (Feb. 9-13, 1997).

McKellop, H. et al., "The Effect of Sterilization Method, Calcium Stearate and Molecular Weight on Wear of UHMWPE Acetabular Cups", Trans. 23$^{rd}$ Ann. Mtg., Soc. Biomaterials, New Orleans, LA, 43 (Apr. 30-May 4, 1997).

McKellop, H. et al., "Effect of Sterilization Method on the Wear Rate of UHMW Polyethylene Acetabular Cups in a Hip Simulator", Trans. 43$^{rd}$ Ann. Mtg., Orthopaedic Res. Soc. San Francisco, CA, 7, 94-16 Feb. 9- 13, 1997.

McKellop, H. et al., "Wear of UHMWPE Acetabular Cups After Gamma Sterilization in Nitrogen, Thermal Stabilization and Artificial Aging", Trans. 23$^{rd}$ Ann. Mtg., Soc. Biomaterials, New Orleans, LA, Apr. 30-May 4, 45 (1997).

Wang, A. et al., "Effect of Radiation Dosage on the Wear of Stabilized UHMWPE Evaluated by Hip and Knee Joint Simulators", Trans. 23$^{rd}$ Ann. Mtg., Soc. Biomaterials, New Orleans, LA, 394 (Apr. 30-May 4, 1997).

Wang, A. et al., "Wear Mechanisms and Wear Testing of Ultra-High Molecular Weight Polyethylene in Total Joint Replacements", Hand-Out for Polyethylene Wear in Orthopaedic Implants Workshop, Trans. 23$^{rd}$ Ann. Mtg., Soc. Biomaterials, New Orleans, LA (Apr. 30-May 4, 1997).

Yu, Y.J. et al., "Oxidation of UHMWPE Acetabular Cups After Sterilization and Wear Testing in a Hip Joint Simulator", Trans. 43$^{rd}$ Ann. Mtg., Orthopaedic Res. Soc. San Francisco, CA, 778 (Feb. 9-13, 1997).

Roe, R. et al., "Effect of Radiation Sterilization and Aging on Ultrahigh Molecular Weight Polyethylene", Journal of Biomedical Materials Research, 15:209-230 (1981).

Li, S. et al., "Chemical Degradation of Polyethylene in Hip and Knee Replacements", 38th Ann. Mtg., Orthopaedic Research Society, Washington, D.C., 41, (Feb. 7-20, 1992).

Kurtz, S.M. et al., "Post-Irradiation Aging and The Stresses in UHMWPE Components for Total Joint Replacement", 40th Ann. Mtg., Orthopaedic Research Society, New Orleans, LA, 584, (Feb. 21-24, 1994).

Lancaster et al., "Friction and Wear", in Jenkins (ed): Polymer Science, 959, 1045, North Holland Publishing Company (1972).

McKellop, H. et al., "Accelerated Aging of Irradiated UHMW Polyethylene for Wear Evaluations", 42nd Annual Meeting, Orthopaedic Research Society, Atlanta, Georgia, 483, (Feb. 19-22, 1996).

Blunn, G.W. et al., "The Effect of Oxidation on the Wear of Untreated and Stabilized UHMWPE", 42nd Annual Meeting, Orthopaedic Research Society, Atlanta, Georgia, 482, (Feb. 19-22, 1996).

"Duration™ Stabilized UHMWPE: an UHMWPE with Superior Wear and Oxidation Resistance; Technical Development and Scientific Evaluation", (Cover sheet and reference page).

Sun, D.C. et al., "The Origin of the White Band Observed in Direct Compression Molded UHMWPE Inserts", 20th Annual Meeting Society for Biomaterials, 121 (Apr. 5-9, 1994).

Sun, D.C. et al., "On the Origins of a Subsurface Oxidation Maximum and its Relationship to the Performance of UHMWPE Implants", 21st Annual Meeting, Society for Biochemicals, San Francisco, CA, 362: (Mar. 18-22, 1995).

Premnath, V. et al., "Melt Irradiated UHMWPE for Total Hip Replacement: Synthesis & Properties", 43rd Annual Meeting, Orthopedic Res. Soc., San Francisco, CA, 91-16, (Feb. 9-13, 1997).

Muratoglu, O.K. et al., "The Effect of Temperature on Radiation Crosslinking of UHMWPE for Use in Total Hip Arthroplasty", 46th Annual Meeting, Orthopaedic Res. Soc., Orlando, FL, 0547 (Mar. 12-15, 2000).

D.C. Sun, C. Stark, J.H. Dumbleton, "Development of an Accelerated Aging Method for Evaluation of Long-term Irradiation Effects on UHMWPE Implants", *Polymer Preprints*, vol. 35, No. 2, pp. 969-970, (1994).

A.F. Booth, "Industrial Sterilization Technologies: New and Old Trends Shape Manufacturer Choices", Medical Device & Diagnostic Industry, pp. 64-72, Feb. 1995.

"Irradiation Effects on Polymers", edited by D.W. Clegg and A.A. Collyer, Elsevier Applied Science, London, (1991).

"Radiation Effects on Polymers", edited by R. L. Clough and S. W. Shalaby, ACS Symposium Series 475, (1991).

P. Eyerer, M. Kurth, H. A. McKellop and T. Mittimeier, "Characterization of UHMWPE hip cups run on joint stimulators", J. Biomedical Materials Research, vol. 21, pp. 275-291, (1987).

A. Wang, D.C. Sun, C.Stark, J.H. Dumbleton, Wear, pp. 181-183:241-249 (1995).

A. Wang, C. Stark, J.H. Dumbleton, "Role of cyclic plastic deformation in the wear of UHMWPE acetabular cups", Journal of Biomedical Materials Research, vol. 29, pp. 619-626, (1995).

Watkins et al."Fractionation of High Density Polyethylene in Propane by Isothermal Pressure Profiling and Isobaric Temperature Profiling" J. Supercritical Fluids, 4:24-31 (1994).

Pleiss et al., "The Improvement of Polyethylene Prostheses Through Radiation Crosslinking", Radiat.. Phys. Chem., 9: 647-652 (1977).

Streicher, "The Behavior of UHMW-PE when Subjected to Sterilization by Ionizing Radiation", Ultra-High Molecular Weight Polyethylene as Biomaterial in Orthopedic Surgery, 66-73 (1990).

Saunders, C. et al., "Radiation Effects on Microorganisms and Polymers for Medical Products", Medical Device & Diagnostic Industry, 222:89-22 (1993).

Kang et al. "The Radiation Chemistry of Polyethylene IX. Temperature Coefficient of Cross-linking and Other Effects", J. Amer. Chem. Society, 89(9): 1980-1986 (1967).

Rose et al., "Radiation Sterilization and the Wear Rate of Polyethylene", J. Orthopaedic Res. Society, 2(4): 393-400(1984).

Oonishi, H. et al., "Super Low Wear Cross-Linked UHMWPE by Heavy High-Dose Gamma Radiation", WPOA 2nd Congress of Hip Section, 61 (1996).

Jahan et al., "Combined chemical and mechanical effects on free radicals in UHMWPE joints during implantation", J. Biomed. Material Res., 25: 1005-1016 (1991).

"Standard Practice for Dosimetry in an Electron Bean Facility for Radiation Processing at Energies Between 300 keV and 25 keV", Am. Soc. for Testing & Materials, Designation: E1649-94, 870-888 (1995).

Oonishi, H. et al., "The Low Wear of Cross-Linked Polyethylene Socket in Total Hip Prostheses", Encyclopedic Handbook of Biomaterials & Bioengineering, vol. 2, Marcel Dekker, Inc., 1853-1868 (1995).

Streicher, R.M., "Investigation on Sterilization and Modification of High Molecular Weight Polyethylenes by Ionizing Irradiation", Beta-gamma, 1/89:34-43.

Swanson, S.A.V. et al., "Chapter 3, Friction, Lubrication and Wear", The Scientific Basis of Joint Replacement, Pittman Medical Publishing Co., Ltd. (1977).

Wang, X. et al., "Melting of Ultrahigh Molecular Weight Polyethylene", J. App. Polymer Sci., 34:593 (1987).

Wright, T.M. et al., "The effect of carbon fiber reinforcement on contact area, contact pressure, and time-dependent-deformation in polyethylene tibial components", J. Biomed. Materials Res., 15:719 (1981).

Zhao, Y. et al., "Effect of Irradiation on Crystallinity and Mechanical Properties of Ultrahigh Molecular Weight Polyethylene", J. Appl. Polym. Sci., 50:1797 (1993).

"News You Can Use", vol. II, No. 2 (May 1996).

"For the Tough Jobs: 1900 UHMW Polymer", Himont, Inc. (1988).

"Abrasion-Resistant 1900 UHMW Polymer", Hercules, Inc. (1979).

"Technical Information: 1900 Ultrahigh Molecular Weight Polymer, General Information and Applications", Bulletin JPE-101A, Hercules, U.S.A., Inc., (1989).

"Technical Information: 1900 Ultrahigh Molecular Weight Polymer, Nuclear Radiation Effects", Bulletin HPE-111, Himont U.S.A., Inc. (1985).

"Technical Information: 1900 Ultrahigh Molecular Weight Polymer, Effect of Polymer Modification", Bulletin HPE-116, Himont U.S.A., Inc. (1987).

"Ultra-High Molecular Weight Polyethylene as Biomaterial in Orthopaedic Surgery", Hogrefe & Huber Publishers.

Appleby, R.W. et al., "Post-gamma irradiation cross-linking of polyethylene tape by acetylene treatment", J. Material Sci., 29: 227-231 (1994).

Higgins, J.C. et al., "Evaluation of Free Radical Reduction Treatments for UHMWPE", Proceedings of the 42nd Annual Mtg., Orthopaedic Res. Soc., Feb. 19-22:485(1996).

Jasty, M. et al., "Marked Improvement in the Wear Resistance of a New Form of UHMWPE in a Physiologic Hip Simulator", Trans. 43rd Ann. Mtg., Orthopaedic Research Soc., San Francisco, CA, Feb. 9-13:785(1997).

Jasty, M. et al., "Marked Improvement in the Wear Resistance of a New Form of UHMWPE in a Physiologic Hip Simulator", Trans. Soc. Biomaterials, vol. XX, p. 71, 23rd Ann. Mtg. Soc. for Biomaterials. New Orleans, Louisiana, U.S.A., Apr. 30-May 4:157 (1997).

Streicher, Influence of Ionizing Irradiation in Air and Nitrogen for Sterilization of Surgical Grade Polyethylene for Implants, Radiat. Phys. Chem., vol. 31, Nos. 4-6: 693-698 (1988).

Roe, R. et al., "Effect of radiation sterilization and aging on ultrahigh molecular weight polyethylene", J. Biomed. Mat. Res., 15: 209 (1981).

Rose, R.M. et al., "On the True Wear Rate of Ultra-High Molecular Weight Polyethylene in the Total Hip Prosthesis", J. Bone & Joint Surgery, 62A(4): 537(1980).

Rose, R.M. et al., "Exploratory Investigations in the Structure Dependence of the Wear Resistance of Polyethylene", Wear, 77:89 (1982).

Rostoker, W. et al., "The Appearances of Wear on Polyethylene—A Comparison of in vivo and in vitro Wear Surfaces", J. Biomed. Materials Res., 12:317 (1978).

Seedhom, B.B. et al., "Wear of Solid Phase Formed High Density Polyethylene in Relation to the Life of Artificial Hips and Knees", Wear, 24: 35 (1973).

Shen, C. et al., "The Friction and Wear Behavior of Irradiated Very High Molecular Weight Polyethylene", Wear, 30:349 (1974).

Shinde, A. et al., "Irradiation of Ultrahigh-Molecular-Weight Polyethylene", J. Polym. Sci., Polym. Phys. Ed., 23: 1681 (1985).

Spruiell, J.E. et al., "Methods of Experimental Physics", L. Marton & C. Marton, Eds., vol. 16, Part B Academic Press, New York (1980).

Streicher, R.M., "Ionizing irradiation for sterilization and modification of high molecular weight polyethylenes" Plastics & Rubber Processing & Applications, 10: 221 (1988).

Oonishi, H. et al., "Improvement of Polyethylene by Irradiation in Artificial Joints", Radiat, Phys. Chem., 39: 495 (1992).

Oonishi, H. et al., "In Vivo and In Vitro Wear Behavior on Weightbearing Surfaces of Polyethylene Sockets Improved by Irradiation in Total Hip Prostheses", Surface Modification Technologies V, 101-115 (1992), Sudarsahn T.S. et al., ed. The Institute of Materials.

Painter, P.C., et al., "The Theory of Vibrational Spectroscopy and its Application to Polymeric Materials", Ed. John Wiley & Sons, New York, U.S.A., (1982).

Paul, J. P., "Forces Transmitted by Joints in the Human Body", Proc. Instn. Mech. Engrs. 181, Part 3J, Paper 8 (1966).

Qu, B.J. et al., "Photocross-linking of Low Density Polyethylene. I Kinetics and Reaction Parameters", J. Appl. Polym. Sci., 48: 701 (1993).

Qu, B.J. et al., "Photocross-linking of Low Density Polyethylene. II Structure and Morphology", J. Appl. Polym. Sci., 48: 711 (1993).

Rimnac, C.M. et al., "Chemical and Mechanical Degradation of UHMWPE: Report of the Development of an In vitro Test", J. Appl. Biomaterials, 5:17 (1994).

Rimnac, C.M. et al., "Observations of Surface Damage and Degradation on Retrieved PCA Knee Implants", Trans. 38th Ann. Orthopaedic Res. Society, Washington, D.C., 330 (1992).

Rinmac, C.M. et al., "Post-Irradiation Aging of Ultra-High Molecular Weight Polyethylene", J. Bone & Joint Surgery, 76-A(7): 1052 (1994).

Atkinson, J. et al., "The nature of silane cross-linked HDPE is discussed. Creep and wear tests indicate its potential as a possible replacement for high molecular weight polyethylene in prostheses", Polymers in Medicine and Surgery, Conf. Held by Plastics and Rubber Institute and Biological Engineering Soc., UK. Sep, P4/1-P4/9 (1986).

Jones, W. et al., Effect of γ Irradiation on the Friction and Wear of Ultrahigh Molecular Weight Polyethylene, Wear 70: 77-92 (1981).

Gent, A. et al., "Elastic Behavior, Birefringence, and Swelling of Amorphous Polyethylene Networks", J. Polymer Sci. 5: 47-60 (1967).

Zoepfl, F. et al., "Differential Scanning Calorimetry Studies of Irradiated Polyethylene: I. Melting Temperatures and Fusion Endotherms", J. Polymer Sci. Polym. Chem. Ed., 22: 2017-2032 (1984).

Zoepfl, F. et al., "Differential Scanning Calorimetry Studies of Irradiated Polyethylene: II. The Effect of Oxygen" J. Polymer Sci. Polym. Chem. Ed., 22: 2032-2045 (1984).

Mandelkern, L. et al., "Fusion of Polymer Networks Formed from Linear Polyethylene: Effect of Intermolecular Order", contribution from the General Electric Research Laboratory and from the Polymer Structure Section, National Bureau of Standards 82: 46-53 (1960).

Muratoglu, O.K. et al., "A Comparison of 5 Different Types of Highly Crosslinked UHMWPES: Physical Properties and Wear Behavior", 45th Annual Meeting, Orthopaedic Research Society, Anaheim, CA, Feb. 1-4, 77 (1999).

Muratoglu, O.K. et al., "A Novel Method of Crosslinking UHMWPE to Improve Wear With Little or No Sacrifice on Mechanical Properties", 45th Annual Meeting, Orthopaedic Research Society, Anaheim, CA, Feb. 1-4, 829 (1999).

Muratoglu, O.K. et al., "Electron Beam Cross Linking of UHMWPE At Room Remperature, A Candidate Bearing Material for Total Joint Arthroplasty", 23rd Annual Meeting of the Society for Biomaterials, New Orleans, Louisana, Apr. 30-May 4, 74 (1997).

Lem, K. et al., "Rheological Properties of Polyethylenes Modified with Dicumyl Peroxide", J. Appl. Polym. Sci., 27: 1367 (1982).

Li, S. et al., "Characterization and Description of an Enhanced Ultra High Molecular Weight Polyethylene for Orthopaedic Bearing Surfaces", Trans. 16th Ann. Soc. Biomaterials Meeting, Charleston, SC, 190 (1990).

Manley, T.R. et al., "The effects of varying peroxide concentration in crosslinked linear polyethylene", Polymer, 12:176 (1971).

McKellop, H. et al., "Friction, Lubrication and Wear of Polyethylene Metal and Polyethylene/Ceramic Hip Prostheses on a Joint Simulator", Fourth World Biomaterials Congress, Berlin, April, 118 (1992).

Minkova, L., "DSC of γ-irradiated ultra-high molecular weight polyethylene and high density polyethylene of normal molecular weight", Colloid & Polymer Sci., 266: 6 (1988).

Minkova, L. et al., "Blends of normal high density and ultra-high molecular weight polyethylene, γ-irradiated at a low dose", Colloid & Polymer Sci., 268: 1018 (1990).

Nagy, E.V. et al., "A Fourier transform infrared technique for the evaluation of polyethylene orthopaedic bearing materials", Trans. 16th Ann. Soc. For Biomaterials Meeting, Charleston, SC 109 (1990).

Narkis, M. et al., "Structure and Tensile Behavior of Irradiation-and Peroxide-Crosslinked Polyethylene", J. Macromol. Sci.-Phys., B26(1): 37 (1987).

Nusbaum, H. J. et al., "The Effects of Radiation Sterilization on the Properties of Ultrahigh Molecular Weight Polyethylene", J. Biomed. Materials Res., 13: 557 (1979).

Grood, E.S. et al., "Analysis of retrieved implants: Crystallinity changes in ultrahigh molecular weight polyethylene", J. Biomedical Materials Res., 16: 399 (1982).

Huang, D.D. et al., "Cyclic Fatigue Behaviors of UHMWPE and Enhanced UHMWPE", Trans. 38th Ann. Mtg., Orthop. Res. Soc., 403 (1992).

Kamel, I. et al., "A Model for Radiation-Induced Changes in Ultrahigh-Molecular-Weight-Polyethylene", J. Polym. Sci., Polym. Phys. Ed., 23:2407 (1985).

Kampouris, E.M. et al., "Benzyl Peroxide as a Crosslinking Agent for Polyethylene", J. Appl. Polym. Sci., 34: 1209 (1987).

Kao, Y.H., "Crystallinity in chemically crosslinked low density polyethylenes: 1 Structural and fusion studies", Polymer, 27:1669 (1986).

Katq, K. et al., "Structural Changes and Melting Behavior of γ-Irradiated Polyethylene", Japanese J. Appl. Phys., 20: 691 (1981).

Kunert, K.A. et al., "Structural investigation of chemically crosslinked low density polyethylene", Polymer, 22: 1355 (1981).

Kurth, M. et al., "Effects of Radiation Sterilization on UHMW-Polyethylene", Trans. Third World Biomaterials Congress, 589 (1988).

Landy, M.M. et al., "Wear of Ultra-high-molecular-weight Polyethylene Components of 90 Retrieved Knee Prostheses", J. Arthroplasty, Supplement, 3: S73 (1988).

deBoer, J. et al., "Crosslinking of Ultra-High Molecular Weight Polyethylene in the Oriented State with Dicumylperoxide", Polymer, 25: 513 (1984).

Dijkstra, D.J. et al., "Cross-linking of ultra-high molecular weight polyethylene in the melt by means of electron bean irradiation", Polymer, 30: 866 (1989).

Ding Z.Y. et al., "Model Filled Polymers. VI. Determination of the Crosslink Density of Polymeric Beads by Swelling," J. Polym. Sci., Part B: Poly. Phys., 29: 1035 (1991).

Eyerer, P. et al., "Property changes of UHMW polyethylene hip cup endoprostheses during implantation", J. Biomed. Materials Res., 18: 1137 (1984).

Eyerer, P., "Polyethylene", Concise Encyclopedia of Medical and Dental Implant Materials, Pergamon Press, Oxford, 271 (1990).

Ferris, B.D., "A quantitiative study of the tissue reaction and its relationship to debris production from a joint implant", J. Exp. Path., 71: 367 (1990).

Gielenz G. et al., "Crystalline and supermolecular structures in linear polyethylene irradiated with fast electrons", Colloid & Polymer Sci., 260: 742 (1982).

Grobbelaar, C.J. et al., "The Radiaion improvement of Polyethylene Prosthesis", J. Bone & Joint Surgery, 60-B(3): 370-374 (1978).

Goodman, S. et al., "Polyethylene wear in knee arthroplasty", Acta Orthop. Scand., 63(3): 358 (1992).

"Poly Two Carbon-Polyethylene Composite-A Carbon Fiber Reinforced Molded Ultra-High Molecular Weight Polyethylene", Technical Report, Zimmer (a Bristol-Myers Squibb Company), Warsaw (1977).

Atkinson, J.R. et al., "Silane cross-linked polyethylene for prosthetic applications. Part I. Certain physical and mechanical properties related to the nature of the material", Biomaterials, 4:267 (1983).

Atkinson, J.R. et al., "Silane cross-linked polyethylene for prosthetic applications. Part II. Creep and wear behavior and a preliminary moulding test", Biomaterials, 5:326 (1984).

Bartel, D.L. et al., "The Effect of Comformity, Thickness, and Material on Stresses In Ultra-High Molecular Weight Components for Total Hip Replacement", J. Bone & Joint Surgery, 68-A(7):1041 (1986).

Bhateja, S.K., "Radiation-Induced Crystallinity Changes In Pressure-Crystallized Ultra-High Molecular Weight Polyethylene", J. Macromol. Sci. Phys., B22(1): 159 (1983).

Bhateja, S.K. et al., "Radiation-Induced Crystallinity Changes in Linear Polyethylene", J. Polym. Sci. Polym. Phys. Ed., 21: 523 (1983).

Bhateja, S.K. et al., "Radiation-Induced Crystallinity Changes in Polyethylene Blends", J. Mater. Sci., 20: 2839 (1985).

Birkinshaw, C. et al., "The Melting Behavior of Irradiated Polymers", Thermochimica Acta, 117: 365 (1987).

Bloebaum, R.D. et al., "Investigation of Early Surface Delamination Observed in Retrieved Heat-Pressed Tibial Inserts", Clin. Orthop., 269: 120 (1991).

Bremmer, T. et al., "Peroxide Modification of Linear Low-Density Polyethylene: A Comparison of Dialkyl Peroxides", J. Appl. Polym. Sci., 49 : 785 (1993).

Brown, K. J. et al., "The Wear of Ultra-High Molecular Weight Polyethylene with Reference to Its Use in Prostheses", Plastics in Medicine & Surgery Plastics & Rubber Institute, London, 2.1 (1975).

Chen, C.J. et al., "Radiation-Induced crosslinking: II. Effect on the crystalline and amorphous densities of polyethylene", Coll. & Polym. Sci.,269: 469 (1991).

Chen, Y.L. et al., "Photocrosslinking of Polyethylene I. Photoinitiators, Crosslinking Agent, and Reaction Kinetics", J. Polym. Sci., Part A: Polym. Chem. 27: 4051 (1989).

Chen, Y.L. et al., "Photocrosslinking of Polyethylene. II. Properties of Photocrosslinked Polyethylene", J. Polym. Sci., Part A; Polym. Chem., 27: 4077 (1989).

Connelly, G.M. et al., "Fatigue Crack Propagation Behavior of Ultrahigh Molecular Weight Polyethylene", J. Orthop. Res., 2: 119 (1984).

deBoer, A.P. et al., "Polyethylene Networks Crosslinked in Solution: Preparation, Elastic Behavior, and Oriented Crystallization. I. Crosslinking in Solution", J. Polym. Sci., Polym. Phys. Ed., 14: 187 (1976).

deBoer, J. et al., "Crosslinking of Ultra-High Molecular Weight Polyethylene in the Melt by Means of 2,5-dimethyl-2,5-bis (tert-butyldioxy)-3-hexyne", Makromol. Chem. Rapid Cornmun., 2: 749 (1981).

deBoer, J. et al., "Crosslinking of Ultra-High Molecular Weight Polyethylene in the Melt by Means of 2,5-dimethyl-2,5-bis (tert-butyldioxy)-3-hexyne: 2. Crystallization Behavior and Mechanical Properties", Polymer, 23: 1944 (1982).

Zachariades, A.E., "A New Class of UHMWPE Orthopaedic Prosthetic Devices with Enhanced Mechanical Properties", Trans. Fourth World Biomaterials Congress, Berlin 623 (1992).

McKellop, H. et al., "Increased Wear of UHMW Polyethylene After Gamma Radiation Sterilization", Trans. 26th Ann. ORS, Atlanta, Georgia, Feb. 5-7, 1980.

McKellop, H., "The Effect of Radiation and Ethylene Oxide Sterilization on the Wear of UHMW Polyethylene", 7th European Conference on Biomaterials, Sep. 8-11, 1987.

B. Hinsch, "Sterilization Methods for Implants Made of UHMWPE", in Ultra-High Molecular Weight Polyethylene as Biomaterials in Orthopedic Surgery, Toronto: Hogrefe & Huber Publishers, pp. 63-65, (1991).

A. Edidin et al., "Enhancement of multiaxial mechanical behavior by slot drawing of UHMWPE: a candidate biomaterial for total knee arthroplasty," 46th Annual Mtg., Orthopaedic. Res. Soc., Mar. 12-15, Orlando, FL (2000).

European Search Report for European Patent Application No. 10156814.5-1219/2191852, Jun. 17, 2010, 6 pages.

Translation of Japanese Office Action and Search Report dated Apr. 13, 2010, relating to Japanese Patent Application 2004-119269.

* cited by examiner

IMPLANTABLE ORTHOPAEDIC DEVICE AND METHOD FOR MAKING THE SAME

FIELD OF THE INVENTION

The present disclosure generally relates to an implantable orthopaedic device and a method for making the same. The present disclosure particularly relates to a polymeric implantable orthopaedic device having a first portion with a first porosity and a second portion with a second porosity, where the first porosity is greater than the second porosity.

BACKGROUND

Implantable orthopaedic devices, such as knee, hip, shoulder, and elbow prostheses, typically include one or more components which are secured to an anchoring bone. Methods for securing such components to the anchoring bone include (i) press-fitting the component to the bone and (ii) the use of a bone cement to secure the component to the anchoring bone. Therefore, in addition to having good biocompatibility characteristics, it is desirable that the materials utilized to fabricate these anchored components possess characteristics which are conducive to these fixation techniques.

Furthermore, some of the components secured to the anchoring bone can include an articulating or bearing surface formed thereon. The bearing surface of these components functions as a surface upon which a natural bone structure or a prosthetic component articulates. Accordingly, in addition to having good biocompatibility and fixation characteristics, the material components having a bearing surface defined thereon should be fabricated from a material which possesses desirable wear characteristics.

In light of the above discussion, an orthopaedic bearing component fabricated from a material which (i) has good biocompatibility characteristics, (ii) possesses characteristics which are conducive to bone fixation techniques, and (iii) has good wear characteristics is desirable.

SUMMARY

An implantable orthopaedic device and a method of preparing an implantable orthopaedic device, such as knee, hip, shoulder, and elbow prostheses, in accordance with the present disclosure comprises one or more of the features or combinations thereof:

A bearing component having a body member. The body member can be sterilized. In addition, the body member of the bearing component can include a polymeric material, such as an organic polymeric material. For example, one or more portions, such as layers, of the body member can be made from a synthetic organic polymeric material made from a synthetic organic polymer. The portions or layers can be made from the same or different polymeric material. Examples of polymeric materials the portions or layers can be made from include ultrahigh molecular weight polyethylene (UHMWPE), crosslinked UHMWPE, and/or Poly(methyl methacrylate) (PMMA). These portions or layers may be secured to one another by any method compatible with implanting the bearing component into the body of an animal. For example, one layer may be mechanically attached to the other layer, or the two layers can be attached with a cement or an adhesive. In addition, the two layers or portions can be integrally attached to one another. One portion (e.g. layer) of the body member may have a porosity which is different than the porosity of another portion (e.g. layer) of the body member. For example, one portion of the body member may have a porosity that is greater than another portion of the body member. In particular, one portion of the member may be porous while another portion of the body member is nonporous, such as a portion that is substantially free of pores. The porous portion of the body member may include polymeric materials such as, for example, UHMWPE and/or high molecular weight PMMA while the nonporous portion of the body member may include a polymeric material such as, for example, UHMWPE or crosslinked UHMWPE. The porous portion or the nonporous portion may have a bearing surface defined thereon. The pores of a porous portion may, for example, be within a size range of about 10 microns to about 400 microns or greater. For example, the pore diameter can be in the range of about 1 to about 2 millimeters. Furthermore, the porosity of the porous portion may be in the range of from about 20% to about 50%. Moreover, the porous portion may have an open porous structure or a closed porous structure.

The method of preparing an implantable orthopaedic device can include securing two polymeric portions (e.g. layers) together, where one polymeric portion includes a porogen and the other polymeric portion does not. The polymeric portions may be made from the same or different polymeric material. Examples of porogens include water soluble (hydrophilic) polymers such as poly(ethylene oxide), poly (vinyl pyrrolidone), and hydroxylethyl cellulose. Further examples of porogens include mineral porogens. In particular, mineral porogens such as salts and other biocompatible minerals can be used as a porogen in the present disclosure. Examples of salt porogens include, but are not limited to, sodium chloride, potassium chloride, and sodium citrate. In addition, amorphous polymers (hydrophobic) can be utilized as a porogen. For example, polyvinyl acetate and/or polystyrene can be utilized as the porogen. In addition, various combinations of porogens can be utilized in the present disclosure. For example, a combination of one or more hydrophilic polymers and one or more salts can be utilized as the porogen in the present disclosure.

Two polymeric portions can be secured together in an integral manner by, for example, compression molding. The portion containing the porogen can be placed in contact with a solvent, for example in an ultra sound bath in the presence of a salt and/or a detergent, so as to cause pores to be formed in this layer while the portion with no porogens remains substantially free of pores. An example of such a solvent is water or an organic solvent. The solvent can be at room temperature, at an elevated temperature, or a cooled temperature, when in contact with the portion containing the porogen. For example, when water is utilized as the solvent it can be at an elevated temperature, for example, about 60° C. to about 70° C. When one or more amorphous polymers are utilized as a porogen, an organic solvent can be used to create the pores. For example, acetone or ethyl acetate can be utilized as the solvent when the porogen includes an amorphous polymer.

In addition, the portion which contains no porogen can be exposed to radiation to cause the crosslinking thereof. For example, the portion which contains no porogen can be exposed to gamma radiation to cause the crosslinking of the polymeric material.

Additional features of the present disclosure will become apparent to those skilled in the art upon consideration of the following detailed description of preferred embodiments exemplifying the best mode of carrying out the subject matter of the disclosure as presently perceived.

DETAILED DESCRIPTION

While the disclosure is susceptible to various modifications and alternative forms, specific embodiments will herein be described in detail. It should be understood, however, that there is no intent to limit the disclosure to the particular forms described, but on the contrary, the intention is to cover all modifications, equivalents, and alternatives falling within the spirit and scope of the disclosure.

The present disclosure generally relates to a polymeric material, for use in the construction of a device to be implanted in the body of an animal (e.g. a human) and associated methods for making the same. The present disclosure particularly relates to implantable polymeric devices such as prosthetic orthopaedic bearings and methods for making the same. Such bearings may be utilized in a number of joint replacement or repair procedures such as surgical procedures associated with the hip, shoulders, knees, ankles, knuckles, or any other joint. For example, such implantable prosthetic bearings may be embodied as a glenoid bearing for implantation into a glenoid of a patient, an acetabular bearing for implantation into an acetabulum of a patient, or a tibial bearing for implantation into a tibia of a patient. A typical prosthetic bearing design includes an articulating or bearing surface on which either a natural bone structure or a prosthetic component articulates. In addition, a prosthetic bearing design may also include an engaging surface which has locking features in the form of mechanisms such as pins, tabs, tapered posts, or the like for locking or otherwise securing the bearing to either another component associated with a prosthetic assembly (e.g., a metal shell or tray) or to the bone itself. As indicated below, bone cement can be utilized in conjunction with these pins, tabs, and/or tapered posts to further facilitate fixation of the bearing to an anchoring bone.

Figure 1:
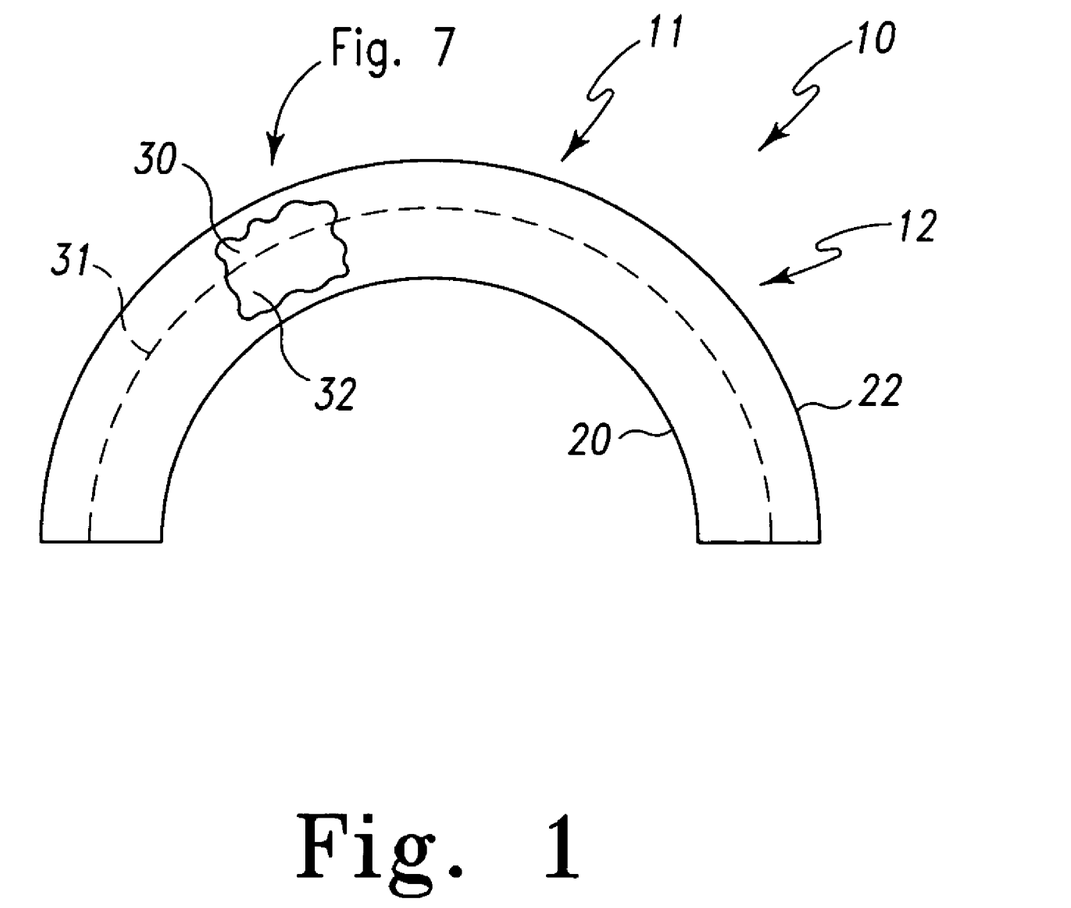
FIG. 1 is a schematic view of an implantable prosthetic bearing that may be produced by processes described herein.
Figure 2:
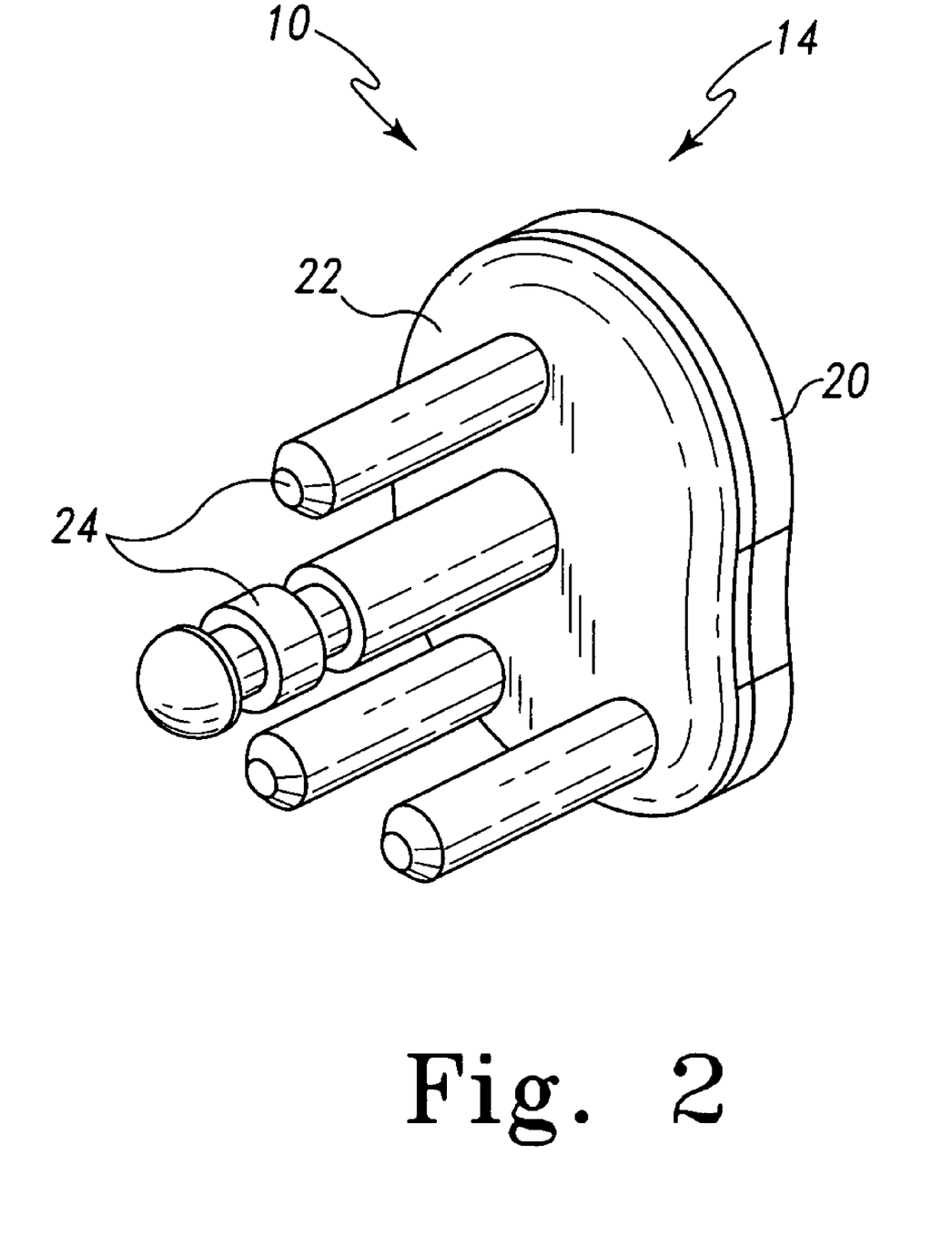
FIG. 2 is a perspective view of an implantable glenoid bearing prosthesis that may be produced by processes described herein.
Figure 3:
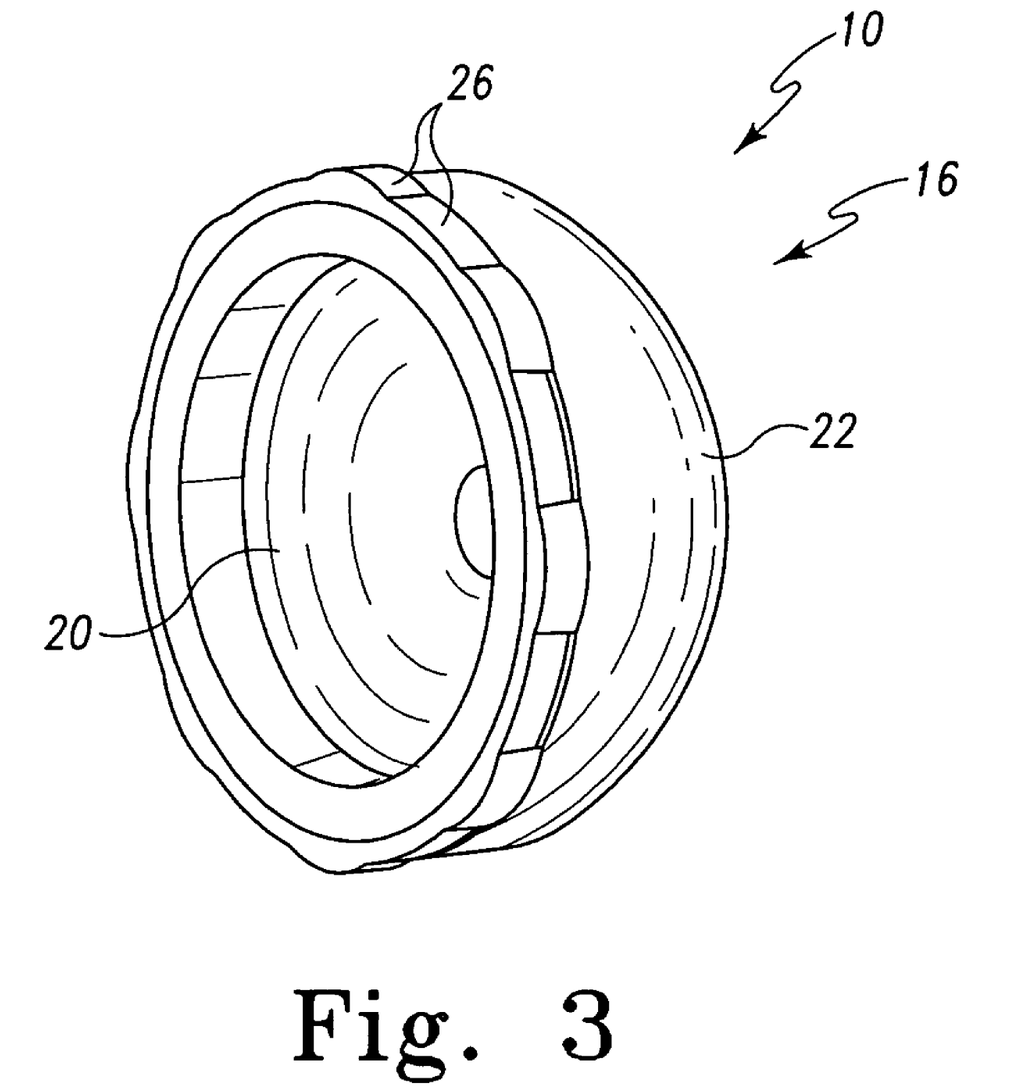
FIG. 3 is a perspective view of an implantable acetabular bearing prosthesis that may be produced by processes described herein.
Figure 4:
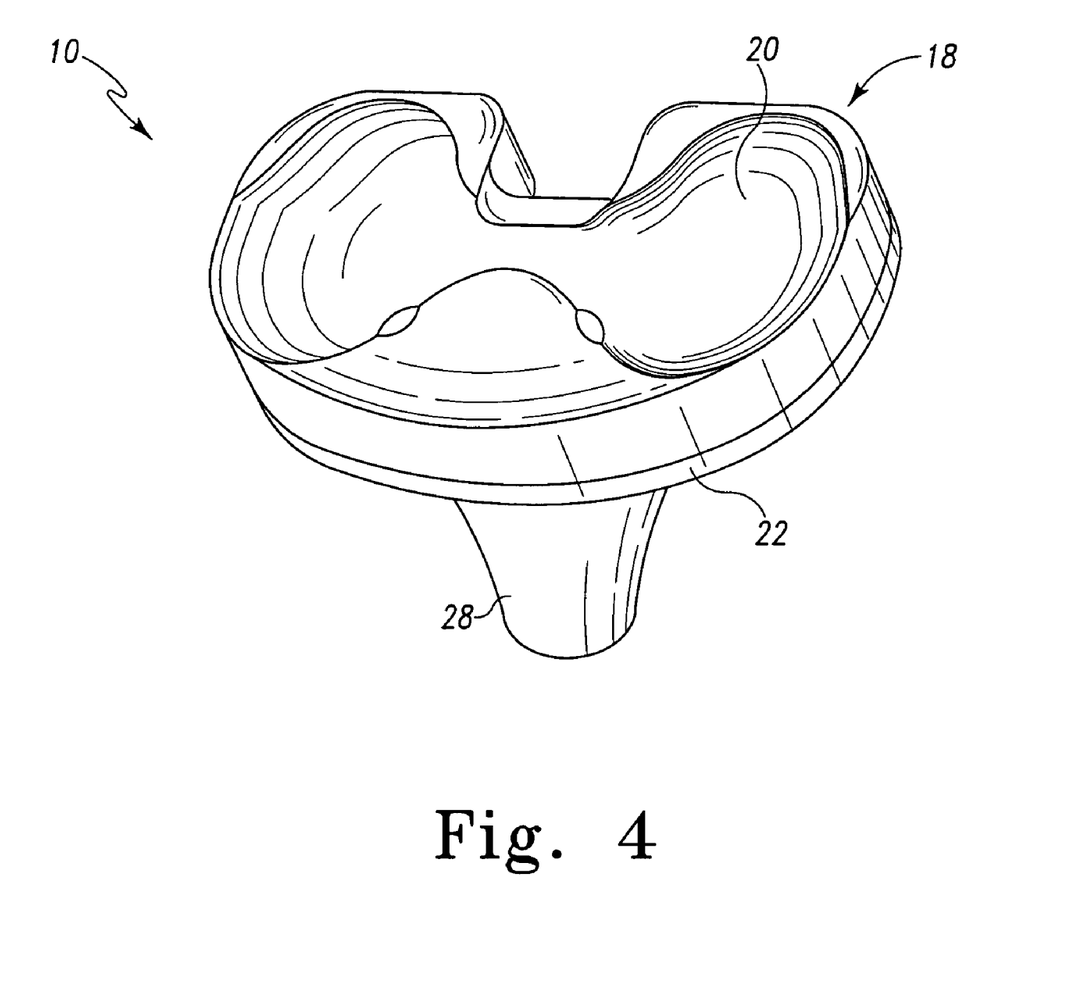
FIG. 4 is a perspective view of an implantable tibial bearing prosthesis that may be produced by processes described herein.

Referring now to FIGS. 1-4, there is shown an implantable polymeric prosthetic bearing component 10 (hereinafter referred to as bearing 10). The bearing 10 is shown schematically as a bearing 12 in FIG. 1, whereas specific exemplary embodiments of the prosthetic bearing 10, such as a glenoid bearing 14 for implantation into a glenoid of a patient (not shown), an acetabular bearing 16 for implantation into an acetabulum of a patient (not shown), and a tibial bearing 18 for implantation into a tibia of a patient (not shown) are shown in FIGS. 2-4, respectively. Each of the embodiments of the prosthetic bearing 10 includes a body member 11 and an articulating or bearing surface 20 on which a natural or prosthetic component bears. For example, in the case of the glenoid bearing 14, a natural or prosthetic humeral head (not shown) bears on the articulating surface 20. Similarly, in the case of a acetabular bearing 16, a natural or prosthetic femoral head (not shown) bears on the articulating surface 20. Moreover, in the case of the tibial bearing 18, a pair of natural or prosthetic femoral condyles (not shown) bear on the bearing or articulating surface 20.

Each of the prosthetic bearings 10 also includes an engaging surface 22 which may have a number of features defined therein for engaging either another prosthetic component or the bone into which the bearing 10 is to be implanted. For example, in the case of the glenoid bearing 14, a number of pins or pegs 24 may be defined in the engaging surface 22 thereof. The pegs 24 are received into a number of corresponding holes (not shown) formed in the glenoid surface of the patient. As previously indicated, the pins 24 can be held in place with the use of bone cement.

In the case of the acetabular bearing 16, a number of keying tabs 26 are defined in the engaging surface 22 along the outer annular surface thereof. The keying tabs 26 are received into a number of corresponding keying slots (not shown) defined in an implanted metal acetabular shell (not shown) in order to prevent rotation of the acetabular bearing 16 relative to the implanted shell. In the case of fixation of the acetabular bearing 16 directly to the acetabulum of the patient (i.e., without the use of a metal shell), the engaging surface 22 of the bearing 16 may alternatively be configured with a number of posts or pegs (not shown) which are received into a number of corresponding holes formed in the patient's acetabulum. In such a case, the posts or pegs can be held in place with the use of bone cement. Moreover, it should be appreciated that the acetabular bearing 16 may be cemented to the patient's acetabulum without the use of posts or pegs on the engaging surface 22 thereof.

In the case of the tibial bearing 18, a tapered post 28 is defined in the engaging surface 22 thereof. The tapered post 28 is received into a corresponding tapered bore (not shown) defined in an implanted tibial tray (not shown) of a knee prosthesis (not shown). It should be appreciated that the engaging surface 22 of the tibial bearing 18 may also be configured with features to allow the tibial bearing 18 to be secured directly to the tibia without the use of an implanted tray (e.g., by use of bone cement).

As indicated above, the bearing (e.g. bearing 10) may be formed from a polymer. As used herein, the term "polymer" is intended to mean any medical grade polymeric material which may be implanted into an animal (e.g. a human patient), including, synthetic organic polymers, such as polyesters, poly(methylmethacrylate), nylon, polycarbonates, and polyolefins. The term "polymer" is also intended to include both homopolymers and copolymers; thus, "polymer" includes a copolymer comprising ethylene and an acrylate derivative, such as methyl methacrylate, methyl acrylate, ethyl methacrylate, ethyl acrylate, and butyl methacrylate.

A specific example of such a polymer is medical grade polyethylene. The term "polyethylene", as defined herein, includes polyethylene, such as a polyethylene homopolymer, high density polyethylene, high molecular weight polyethylene, high density high molecular weight polyethylene, or any other type of polyethylene utilized in the construction of a prosthetic implant. A more specific example of such a polymer is medical grade ultrahigh molecular weight polyethylene (UHMWPE).

The starting materials (e.g., polymers and copolymers) may be provided as powders or a preform. What is meant herein by the term "powder" is resin particles sometimes referred to as "flakes". Preforms and powders may be provided in a number of different pre-treated or preconditioned variations. For example, crosslinked or non-crosslinked (e.g., irradiated or non-irradiated) powders may be utilized. In particular, it may be desirable for a manufacturer of an orthopaedic implant, such as prosthetic bearings, to purchase material (e.g. polyethylene flakes) which has been irradiated (or otherwise crosslinked), pre-quenched, or otherwise preconditioned by a commercial supplier or other manufacturer of the material. Such "out-sourcing" of preconditioning processes is contemplated for use in the processes described herein. On the other hand, it is also contemplated that the polymeric material is not irradiated (or otherwise crosslinked), quenched, or otherwise conditioned until after the flakes have been consolidated (e.g. by compression molding) into a structure, such as a polymeric puck.

As indicated above, the polymer utilized in the construction of a device for implanting in the body of an animal, e.g. implantable orthopaedic device such as a bearing, may be crosslinked by, for example, exposure to radiation such as gamma radiation. Such exposure may be in the exemplary range of 0.5-150 Mrads. However, it should be appreciated that the concepts described herein may be utilized in conjunction with non-crosslinked polymeric materials. A specific example of a crosslinked polymeric material that can be utilized in the construction of a device to be implanted in the body of an animal, such as the bearings described herein, is crosslinked UHMWPE. As alluded to above, crosslinked UHMWPE can be obtained by irradiating non-crosslinked UHMWPE with gamma radiation. Examples of commercially available non-crosslinked UHMWPE which can be irradiated to obtain crosslinked UHMWPE include GUR® 1050 (having a molecular weight of about 5 million to about 6 million) and GUR® 1020 (having a molecular weight of about 3 million to about 4 million) both of which are available from Ticona, located in Summit, N.J. An additional example of crosslinked UHMWPE includes, but is not limited to, that disclosed in U.S. Pat. No. 6,316,158 B1 entitled "Process for Medical Implant of Cross-Linked Ultrahigh Molecular Weight polyethylene Having Improved Balance of Wear Properties and Oxidation Resistance", which was issued on Nov. 13, 2001, to Saum et al. which is incorporated herein by reference.

As indicated above, one manner by which polymers are crosslinked is by gamma irradiation, although other manners such as electron beam or X-ray radiation may also be used. The polymer may be irradiated with gamma radiation at a dose from about 0.5 Mrads to about 150 Mrads, illustratively from about 3 to about 50 Mrads, and illustratively from about 3 to about 15 Mrads using methods known in the art. The irradiation process may be optionally performed under vacuum or in an inert or substantially oxygen-free atmosphere by placing the bearing, preform, porous structure, or powder in a bag. Such a bag may be constructed from materials including, for example, aluminum foil, polyethylene, and the like which are suitable for such irradiation processes. The bag may be optionally evacuated and the atmosphere substantially replaced with an inert gas such as nitrogen, argon, and the like. It will be appreciated, however, that acceptable results may be achieved for certain bearing or material configurations when the irradiation process is carried out under atmospheric conditions, i.e., with some oxygen present. (Note that irradiation of polymers (e.g., UHMWPE) is utilized not only for crosslinking of the material, but also for sterilization purposes. Typically, the irradiation dose used for crosslinking is higher than the irradiation dose used for sterilization).

Figure 7:
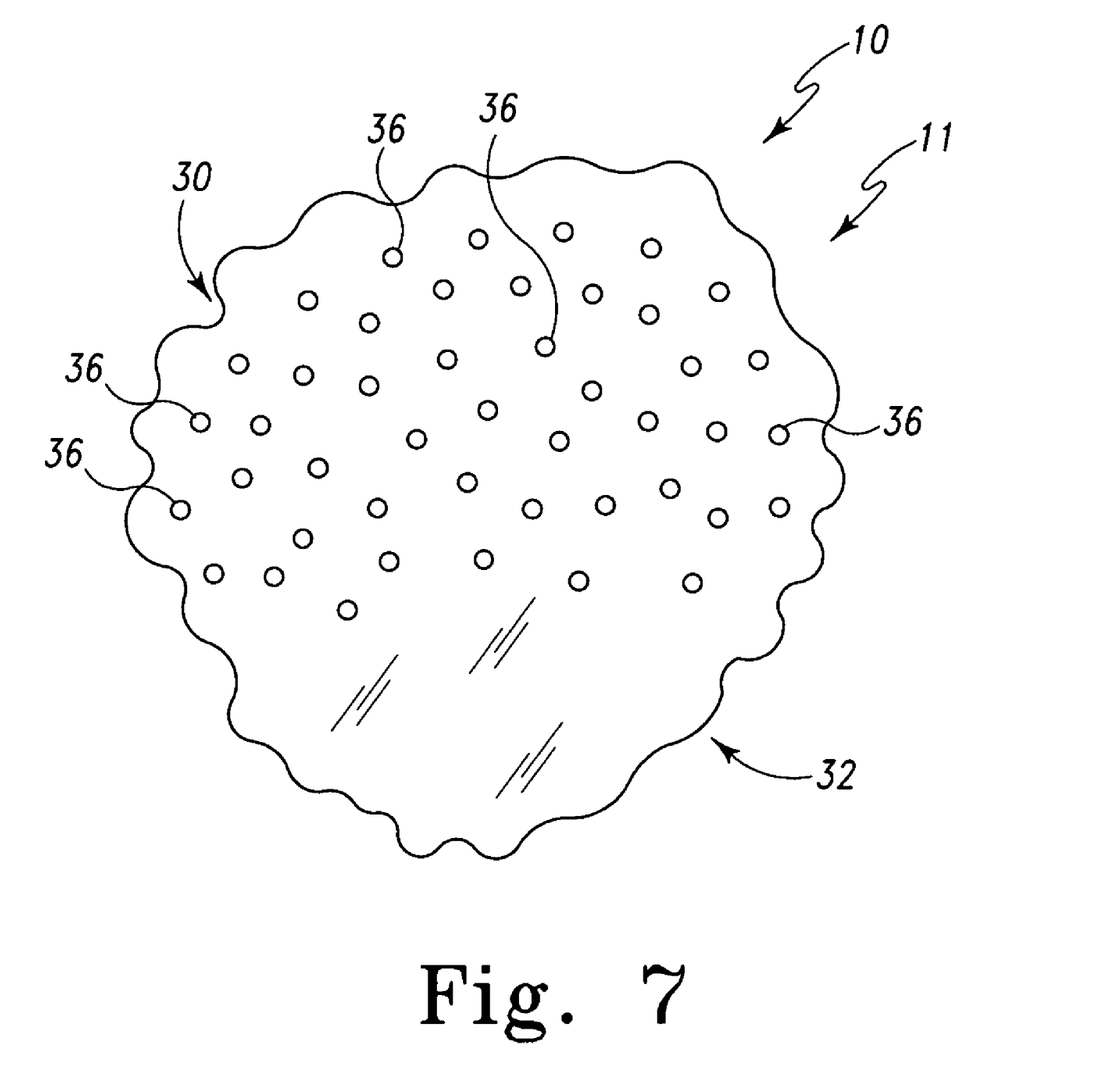
FIG. 7 is an enlarged fragmentary schematic view of a portion of FIG. 1 which is encircled and indicated as FIG. 7 showing a porous polymeric portion secured to a nonporous polymeric portion.

As previously indicated, the bearing 10 may be formed from a polymer, such as an organic polymer. In particular, the body member 11 of the bearing 10 may be formed from one or more organic polymer layers secured or attached to one another. It is contemplated that the layers may be made from the same or different polymer materials. For example, FIG. 7 is an enlarged fragmentary schematic view of a portion of the bearing 10 shown in FIG. 1. As shown in FIG. 7, body member 11 of bearing 10 includes two polymeric layers, i.e. a polymeric layer 30 attached to a polymeric layer 32. (Note that FIG. 1 shows a schematic phantom line 31 interposed between polymeric layers 30 and 32.) It is contemplated that the two polymeric layers can be attached to one another by any method compatible with the bearing being implanted into the body of an animal. For example, the two layers can be attached by mechanically securing the polymeric layers together, by securing the polymeric layers together with a cement or an adhesive, or integrally attaching the two layers together. Furthermore, while body member 11 includes two polymeric layers, it is contemplated that a body member 11 of the present disclosure may include more than two polymeric layers. As previously stated, layers 30 and 32 may be made from the same or different polymeric materials. As discussed above, examples of polymeric materials layers 30 and 32 can be made from include ultrahigh molecular weight polyethylene (UHMWPE), crosslinked UHMWPE, PEEK, and/or Poly(methyl methacrylate) (PMMA). In addition, each layer 30 and 32 may be a blend of one or more polymeric materials.

Figure 5:
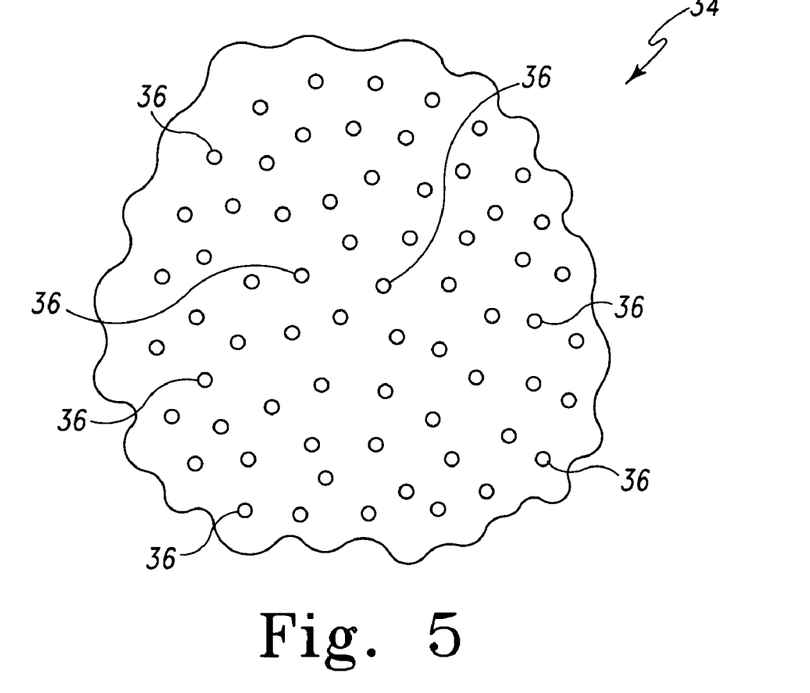
FIG. 5 is a schematic representation of a porous polymeric material showing the pores defined therein.
Figure 6:
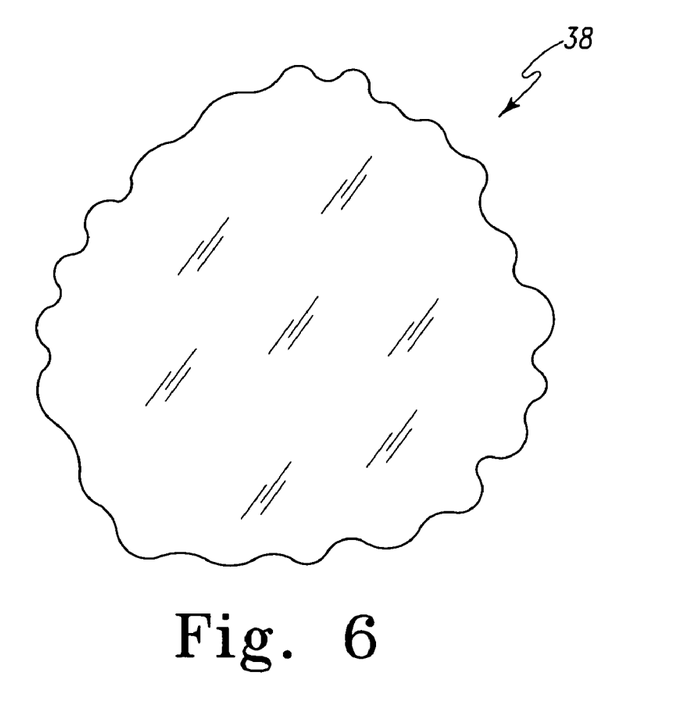
FIG. 6 is a schematic representation of a nonporous polymeric material.

Still referring to FIG. 7, it can be seen that the layer 30 of body member 11 has a porosity which is different from the porosity of layer 32. In particular, layer 30 is porous while layer 32 is substantially nonporous, i.e. layer 32 is substantially free of pores. What is meant herein by a portion or layer being "substantially free of pores" is that the portion or layer has a de minimis amount of pores defined therein which would be present as a result of the layer being processed in a conventional manner. For example, a polymeric layer that has not been deliberately subjected to a process that substantially increases the layer's porosity will have a de minimis amount of pores defined therein, and thus will be "substantially free of pores." Schematic representations of exemplary polymeric layers in which one is "substantially free of pores" and one is "porous" are respectively shown in FIGS. 6 and 5, respectively. As shown in FIG. 5, porous polymeric layer 34 has a plurality of pores 36 defined therein. On the other hand, as shown in FIG. 6, polymeric layer 38, which is substantially free of pores, has a de minimis amount of pores defined therein. However, there are processes a polymeric material or layer can be subjected to in order to increase its porosity. As discussed in greater detail below, one example of a process a polymeric material or polymeric layer can be subjected to for the purpose of increasing its porosity includes embedding a porogen in the polymeric material or layer, and then contacting the material or layer with a solvent of the porogen to cause the formation of pores. A nonporous layer, or one which is substantially free of pores, includes polymeric layers that are made from polymeric material which is not subjected to a process that includes embedding a porogen into the material and then extracting the porogen with a solvent for the purpose of increasing its porosity, since a layer made from such a material will be substantially free of pores.

Nonporous layer 32 can be made from, for example, UHMWPE or crosslinked UHMWPE. In addition, as shown in FIG. 1, layer 32 can have a bearing surface 20 defined thereon. As discussed above, bearing surface 20 functions as a surface upon which either a natural bone structure or a prosthetic component articulates.

Now turning to layer 30 shown in FIG. 7, as indicated above this layer is porous. In particular, layer has a plurality of pores 36 defined therein. For example, a substantial portion of the pores of layer 30 can be within a size range of about 10 microns in diameter to about 400 microns in diameter. The porosity of layer 30 can be in the range from about 20% porosity to about 50% porosity. In addition, layer 30 can have an open porous structure or a closed porous structure. In the alternative, a portion of layer 30 can have an open porous structure, while another portion of layer 30 has a closed porous structure. Like nonporous layer 32, porous layer 30 is made from organic polymeric materials such as, for example, UHMWPE and/or PMMA.

One exemplary method of fabricating an implantable organic polymeric orthopaedic device having a polymer layer with a porosity that is different from another polymer layer includes securing two polymeric portions (e.g. layers) together, where one polymeric portion includes a porogen and the other polymeric portion does not. For example, the two polymeric portions can be secured together in an integral manner via compression molding the two portions together. The portion containing the porogen is contacted with a solvent so as to cause the porogen to be extracted from the portion and thus cause pores to be formed in this layer, while the portion with no porogens remains substantially free of pores. An example of such a solvent is water, while examples of porogens that can be extracted with water include hydrophilic polymers such as poly(ethylene oxide), poly(vinyl pyrrolidone), poly(hydroxyethyl methacrylate), carboxyethyl cellulose, poly(vinyl alcohol), and hydroxylethyl cellulose. Further examples of water extractable porogens include biocompatible minerals, such as salts. Examples of salt porogens include, but are not limited to, sodium chloride, potassium chloride, potassium citrate, sodium carbonate, and sodium citrate. It is contemplated that a combination which includes a hydrophilic polymer and a salt can be used as a porogen in the present disclosure. Amorphous polymers (hydrophobic) can also be utilized as a porogen. Examples of amorphous polymers include polyvinyl acetate and polystyrene. Furthermore, low melting point semi-crystalline polymers can be used as a porogen in a layer of UHMWPE. All of these porogens can be extracted from a polymeric layer, such as UHMWPE or PMMA, so as to cause the formation of pores, without dissolving the polymeric layer itself.

The particular solvent utilized to extract a porogen from a polymeric layer will depend upon the solubility characteristics of the porogen present. For example, when the porogen is hydrophilic, water can be used as the solvent. When the porogen is hydrophobic, an organic solvent such as an alcohol and/or acetone and/or ethyl acetate can be utilized. Furthermore, the particular conditions utilized for the extraction will also depend upon the solubility characteristics of the porogen present. For example, when water is utilized to extract a porogen it can be heated to an elevated temperature; be at room temperature; or be cooled below room temperature (e.g. when a porogen exhibits inverse temperature solubility characteristics), depending upon the solubility characteristics of the porogen. For example, water heated to a temperature in the range of about 60° C. to about 70° C. can be used as a solvent in the present disclosure. In addition, the extraction of a porogen with an appropriate solvent can performed in an ultra sound bath. Moreover, a solvent, such as water, can have an amount of salt (e.g. sodium chloride) and/or a detergent present therein to inhibit the formation of a gel by the porogen being extracted from polymeric layer.

Extraction of the polymeric layer containing the porogen should take place for a time period to allow the removal of a sufficient amount of the porogen so as to cause the formation of a desired amount of pores. In other words, extraction should take place in a manner so as to result in the layer having the desired porosity. For example, the extraction conditions can be such that essentially all of the porogen is removed from the polymeric layer. Accordingly, any porogen remaining in the extracted layer should be a de minimus amount, and have no significant biological effect on the tissue of the animal the polymeric layer is implanted into. The specific extraction parameters, for example, the solvent(s) used, the extraction time period, and the temperature, to achieve a particular desired porosity will depend, at least in part, upon the solubility characteristics of the porogen imbedded in the polymeric layer. Accordingly, in light of the discussion set forth herein, the extraction parameters utilized to obtain a polymeric layer having a desired porosity will be determined for each particular application.

As an illustrative example, a polymeric work piece having a polymer layer with a porosity that is different from another polymer layer can be produced in the following manner. A layer of porogen free polymeric material, such as a layer of porogen free UHMWPE flakes, is placed into the mold of a compression molding apparatus. In the alternative a porogen free preform of crosslinked UHMWPE serves as a layer and is placed into the mold of the compression molding apparatus. A blend of a polymeric material flakes, such as UHMWPE or high molecular weight poly(methyl methacrylate) and a porogen is then placed as a layer onto the aforementioned porogen free polymer layer. For example, the polymeric material/ porogen blend can include dry blending UHMWPE flake with a melt-processable, water soluble (hydrophilic) polymer powder. Alternatively, the blend containing a porogen can include a dry blend of UHMWPE flake with a combination of a melt-processable, water soluble polymer and a water soluble mineral and poly(ethylene oxide). Furthermore, the blend containing a porogen can include a dry blend of UHMWPE flake with a combination of powder of two different water soluble polymers, one of them being melt processable. The use of a mineral and a non-melt processable, water soluble polymer in the porogen blend results in the formation of relatively larger pores. As discussed above, melt-processable, water-soluble polymers which can be utilized include, but are not limited to, poly(ethylene oxide) and poly(vinyl alcohol). The poly(vinyl alcohol) can, for example, have a degree of hydrolysis of about 70% to about 90%. As indicated above, water soluble mineral porogens include, but are not limited to, potassium citrate and sodium carbonate.

The amount of porogen to add to a particular work piece is dependent upon what degree of porosity is desired. For example, amounts of a hydrophilic polymer porogen (e.g. poly(ethylene oxide)) equivalent to about 2%, 5%, 15%, or 20% of the volume of the entire work piece can be added to the porous layer to obtain work pieces having different degrees of porosities. Illustratively, if a work piece having a porosity of about 20% is desired, an amount of a hydrophilic polymer porogen (e.g. poly(ethylene oxide)) equivalent to about 20% of the volume of the entire work piece can be added to the porous layer (volume percentages can be calculated based upon the density of the components). In the alternative, if a work piece having a porosity of about 20% is desired, and a combination of a hydrophilic polymer (e.g. poly(ethylene oxide)) and a mineral (e.g. sodium chloride) is going to be utilized as the porogen, then an amount of the hydrophilic polymer and a mineral equivalent to about 2% and 18%, respectively, of the volume of the entire work piece is added to the porous layer. In another illustration, if a work piece having a porosity of about 30% is desired, an amount of a hydrophilic polymer porogen (e.g. poly(ethylene oxide)) equivalent to about 30% of the volume of the entire work piece can be added to the porous layer (volume percentages can be calculated based upon the density of the components). Once again, if a work piece having a porosity of about 30% is desired, and a combination of a hydrophilic polymer (e.g. poly(ethylene oxide)) and a mineral (e.g. sodium chloride) is going to be utilized as the porogen, then an amount of the hydrophilic polymer and a mineral equivalent to about 2% and 28%, respectively, of the volume of the entire work piece is added to the porous layer. The above described approach can be utilized to create work pieces having a wide range of desired porosities.

Addition of a mineral porogen allows control over the size of the pores, since pore size is a function of the size of the mineral crystal. For example, when sodium chloride is used as the porogen, a fine grade salt crystal will generally result in smaller diameter pores as compared to when a medium or coarse grade salt crystal is used. For example, with a coarse grade salt crystal pore diameters in the millimeter range, such as about 1 to about 2 millimeter diameter pores, can be created as opposed to about 10 micron to about 400 micron diameter pores obtained with no salt porogen or salt porogens with a finer grade. When a hydrophilic polymer porogen is used alone, or in the absence of a mineral porogen, the pores created tend to be smaller (e.g. diameters of about 200 microns). However, the use of a hydrophilic polymer porogen enhances the degree of connectivity between the pores created, and thus results in a work piece having an open porous structure being obtained. Accordingly, the combination of a hydrophilic polymer porogen used in conjunction with a mineral porogen tends to result in a work piece having an open porous structure with somewhat larger pore size. In light of the discussion set forth herein, the amount and type of a porogen, or combination of porogens, used to obtain a work piece having a desired porosity will be determined for each particular application.

Once the mold of the compression molding apparatus contains a layer of a porogen free polymeric material (e.g. as flakes or a preform) in contact with a layer of polymeric material/porogen(s) blend. Both layers are then compression molded in a well known conventional manner to cause the formation of a single solid polymeric work piece in which one layer of the work piece is made of a porogen free polymeric material and the other, integrally attached, layer is made of a polymeric material/porogen blend. After compression molding in the above described manner, the work piece is placed in contact with a solvent for the porogen, so as to cause the porogen to be solubilized and extracted from the work piece. For example, in the case where poly(ethylene oxide) is the porogen, water can be utilized as the solvent. The solubilization and extraction of the porogen causes pores to be formed in the layer of the work piece where the porogen was located, while the porogen free layer remains substantially free of pores. Accordingly, the result is a work piece made of organic polymeric material in which the work piece has one layer that has a porosity that is different from the porosity of the other layer. In particular, one layer is nonporous, or substantially free of pores, and the other layer is porous.

The above described procedure can be utilized to prepare a porous structure or work piece which can be used in the preparation of an orthopaedic device for cemented fixation to an anchoring bone. In particular, a layer of UHMWPE flakes is disposed into a mold of a compression molding apparatus. A blend of a UHMWPE and poly(ethylene oxide) (i.e. the porogen) flakes is then placed as a layer onto the aforementioned UHMWPE layer. As indicated above, both layers are then compression molded in a well known conventional manner to cause the formation of a single solid polymeric work piece in which one layer of the work piece is made of UHMWPE and the other, integrally attached, layer is made of the UHMWPE/poly(ethylene oxide) blend. If desired, at this point the work piece can be exposed to, for example, gamma radiation in the manner described above to cause crosslinking of the UHMWPE. After crosslinking, the work piece can be melt quenched if desired. The work piece is then placed in contact with, for example, water so as to cause the poly(ethylene oxide) to be solubilized and extracted from the work piece. As previously indicated, the solubilization and extraction of the poly(ethylene oxide) causes pores to be formed in the layer of the work piece where the poly(ethylene oxide) was located, while the layer of UHMWPE containing no poly(ethylene oxide) remains substantially free of pores.

The above described procedure can also be utilized to prepare a porous structure or work piece which can be used in the preparation of an orthopaedic device for press-fit fixation to an anchoring bone. In particular, a layer of UHMWPE flakes is disposed into a mold of a compression molding apparatus. A blend of poly(ethylene oxide), sodium chloride, and UHMWPE flakes is then placed as a layer onto the aforementioned UHMWPE layer. Both layers are then compression molded in a well known conventional manner to cause the formation of a single solid polymeric work piece in which one layer of the work piece is made of UHMWPE and the other, integrally attached, layer is made of the poly(ethylene oxide)-sodium chloride-UHMWPE blend. If desired, at this point the work piece can be exposed to, for example, gamma radiation in the manner described above to cause crosslinking of the UHMWPE. After crosslinking, the work piece can be melt quenched if desired. The work piece is then placed in contact with, for example, water so as to cause the poly(ethylene oxide) and sodium chloride to be solubilized and extracted from the work piece. The solubilization and extraction of the poly(ethylene oxide) causes pores to be formed in the layer of the work piece where the poly(ethylene oxide) was located, while the layer of UHMWPE containing no porogen remains substantially free of pores.

The above described work pieces, either pre or post extraction, are molded, machined, or otherwise shaped or formed into an orthopaedic device, for example a bearing, such as bearing 10, a net-shape bearing, or a near net-shape bearing for implanting into the body of an animal. What is meant herein by the term "net-shape bearing" is a bearing that is in a shape or condition that is satisfactory for use in a prosthetic implant upon removal of the bearing from a fabrication tool without requiring any additional machining. The term "near net-shape bearing", on the other hand, is meant herein to define a bearing which requires a small degree of further manipulation, such as polishing or smoothing, to produce the final bearing.

Having a porous polymeric layer included in a polymeric orthopaedic device for implanting into the body of an animal, enhances bone cement bonding to the anchoring bone. For example, the porous polymeric layer allows bone cement incursion into the pores and thus enhances fixation to the anchoring bone. Accordingly, the polymeric orthopaedic devices of the present disclosure have good biocompatibility characteristics, possess characteristics which are conducive to bone fixation techniques, and have good wear characteristics.

Example

The following example illustrates the formation of a porous UHMWPE work piece or layer without an attached layer of a nonporous polymeric material. However, it should be understood that the following procedure for obtaining a porous UHMWPE layer can be utilized in conjunction with the above described compression molding procedures to obtain a single work piece having a porous polymeric layer attached to a nonporous layer.

A dry blend of 13.46 grams of poly(ethylene oxide) having a molecular weight of about 7,000,000 (commercially available from Dow Chemical Co., located in Midland, Mich.) and 24.60 grams of GUR 1020 (commercially available from Ticona, located in Auburn Hills, Mich.) was compression molded into a solid work piece. The compression molding process utilized a melt temperature of about 320° F. to about 350° F., a consolidation pressure of about 1200 psi to about 1600 psi, and a soak time of about 10 minutes to about 20 minutes. The solid work piece was then extracted with room temperature water for a period of one to two days or until about 95% to about 100% of the water soluble polymer, i.e. poly(ethylene oxide), was removed from the work piece. Utilization of this procedure results in an interconnected porous structure, with a porosity volume from about 20% to about 50%, and a pore size ranging from about 10 microns in diameter to about 400 microns in diameter. However, the specific procedure set forth in this example resulted in a porosity of about 30%.

While the invention has been illustrated and described in detail in the foregoing description, such an illustration and description is to be considered as exemplary and not restrictive in character, it being understood that only the illustrative embodiments have been described and that all changes and modifications that come within the spirit of the invention are desired to be protected.

There are a plurality of advantages of the present invention arising from the various features of the prosthetic bearing and methods of making the same described herein. It will be noted that alternative embodiments of each of the prosthetic bearings and methods of making the same of the present invention may not include all of the features described yet benefit from at least some of the advantages of such features. Those of ordinary skill in the art may readily devise their own implementations of prosthetic bearings and methods of making the same that incorporate one or more of the features of the present invention and fall within the spirit and scope of the present invention.

The invention claimed is:

1. An implantable orthopaedic bearing, consisting of:
a polymeric body member defining a structure selected from the group consisting of (i) an acetabular bearing configured to be implanted into an acetabulum of a patient, (ii) a glenoid bearing configured to be implanted into a glenoid of a patient, and (iii) a tibial bearing configured to be implanted into a tibia of a patient, the body member having a first portion and a second portion, the second portion being integrally attached to the first portion, wherein (i) the first portion of the polymeric body member has a plurality of pores defined therein, (ii) the second portion of the polymeric body member is substantially free of pores, and (iii) the second portion of the polymeric body member has a surface that defines a concave articulating surface upon which a natural or prosthetic component bears.

2. The implantable orthopaedic bearing of claim 1, wherein:
the porosity of the first portion of the polymeric body member is from about 20% to about 50%.

3. The implantable orthopaedic bearing of claim 2, wherein:
a substantial portion of the pores of the first portion have a diameter in range of from about 10 microns to about 400 microns.

4. The implantable orthopaedic bearing of claim 3, wherein:
the first portion has an open porous structure.

5. The implantable orthopaedic bearing of claim 1, wherein:
the polymeric body member is sterile.

6. An implantable orthopaedic device, consisting of:
a polymeric bearing component selected from the group consisting of (i) an acetabular bearing component configured to be implanted into an acetabulum of a patient, (ii) a glenoid bearing component configured to be implanted into a glenoid of a patient, and (iii) a tibial bearing component configured to be implanted into a tibia of a patient, the polymeric bearing component having a first layer attached to a second layer, wherein (i) the second layer has a concave articulating surface upon which a natural or prosthetic component bears defined thereon, (ii) the first layer has a first porosity, (iii) the second layer has a second porosity, and (iv) the first porosity is greater than the second porosity.

7. The implantable orthopaedic device of claim 6, wherein:
the first layer of the polymeric bearing component includes UHMWPE.

8. The implantable orthopaedic device of claim 6, wherein:
the second layer of the polymeric bearing component includes crosslinked UHMWPE.

9. The implantable orthopaedic device of claim 8, wherein:
porosity of the first layer of the polymeric bearing component is from about 20% to about 50%.

10. The implantable orthopaedic device of claim 8, wherein:
the first layer has pores within a size range of from about 10 microns in diameter to about 400 microns in diameter.

11. The implantable orthopaedic device of claim 6, wherein:
the first layer of the polymeric bearing component includes UHMWPE, and
the second layer of the polymeric bearing component includes crosslinked UHMWPE.

12. The implantable orthopaedic device of claim 6, wherein:
the first layer of the polymeric bearing component includes PMMA.

13. The implantable orthopaedic device of claim 6, wherein:
the first layer of the polymeric bearing component includes PMMA, and
the second layer of the polymeric bearing component includes crosslinked UHMWPE.

14. The implantable orthopaedic device of claim 6, wherein:
the first layer of the polymeric bearing component has an open porous structure.

* * * * *